United States Patent
Honold et al.

(10) Patent No.: US 7,189,732 B2
(45) Date of Patent: Mar. 13, 2007

(54) PYRIDO[2,3-D]PYRIMIDINE DICHLORO-PHENYL DERIVATIVES

(75) Inventors: Konrad Honold, Penzberg (DE); Wolfgang Schaefer, Mannheim (DE); Stefan Scheiblich, Penzberg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 11/079,623

(22) Filed: Mar. 14, 2005

(65) Prior Publication Data

US 2006/0014765 A1   Jan. 19, 2006

(30) Foreign Application Priority Data

Mar. 15, 2004 (EP) .................... 04006051

(51) Int. Cl.
*A01N 43/90* (2006.01)
*A61K 31/519* (2006.01)
*C07D 471/00* (2006.01)

(52) U.S. Cl. .................. 514/264.11; 544/279

(58) Field of Classification Search ............ 514/234.2, 514/252.16, 264.11; 544/122, 123, 279
See application file for complete search history.

(56) References Cited

FOREIGN PATENT DOCUMENTS

| WO | WO 96/15128 | | 5/1996 |
| WO | WO/1996/15128 | * | 5/1996 |
| WO | WO 02/090360 | | 11/2002 |
| WO | WO/2002/090360 | * | 11/2002 |
| WO | WO 03/000011 | | 1/2003 |

OTHER PUBLICATIONS

Margaret C. Frame, Biochimica et Biophysica Acta-Reviews on Cancer, vol. 1602, Issue 2, Jun. 21, 2002, pp. 114-130.*
Wolff, Manfred E. "Burger's Medicinal Chemistry, 5ed, Part I,", John Wiley & Sons, 1995, pp. 975-977.*
Banker, G.S. et al, "Modern Pharmaceutics, 3ed.", Marcel Dekker, New York, 1996, pp. 451 and 596.*
Noble, M.E.M. et al, Science, vol. 303, pp. 1800-1805.*
Bastin et al., Organic Proc. Res. Dev., 4, pp. 427-435 (2000).
Biscardi et al., Adv. Cancer Res., 76, pp. 61-119 (2000).
Merrifield, Fed. Proc. Fed. Amer. Soc. Exp. Biol., 21, pp. 412 (1962).
Susa et al., Trends Pharmacoal. Sci., 21, pp. 489-495 (2000).

* cited by examiner

*Primary Examiner*—Deepak Rao
*Assistant Examiner*—Cecilia Jaisle
(74) *Attorney, Agent, or Firm*—George W. Johnston; Patricia S. Rocha-Tramaloni; Brian C. Remy

(57) ABSTRACT

The invention describes compounds of the general formula I

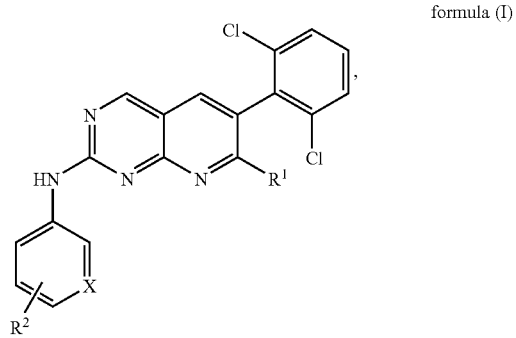

formula (I)

a process for their manufacture, compositions containing them and their manufacture as well as the use of these compounds as pharmaceutically active agents. These compounds show activity as protein kinase inhibitors, in particular src family tyrosine kinase inhibitors, and may therefore be useful for the treatment of diseases mediated by said tyrosine kinases.

16 Claims, No Drawings

PYRIDO[2,3-D]PYRIMIDINE DICHLORO-PHENYL DERIVATIVES

PRIORITY TO RELATED APPLICATIONS

This application claims the benefit of European Application No. 04006051.9, filed Mar. 15, 2004, which is hereby incorporated herein by reference in its entirety.

BACKGROUND OF THE INVENTION

1. Field of the Invention

The present invention relates to novel, bicyclic pyrido[2,3-d]pyrimidines, to a process for their manufacture, compositions containing them and their manufacture as well as the use of these compounds as pharmaceutically active agents for the treatment of diseases mediated by tyrosine kinases including inflammatory diseases, immunological diseases, CNS diseases, oncological diseases, and bone diseases.

2. Description of Related Art

Some substituted bicyclic nitrogen heterocycles are known in the art for their protein kinase and tyrosine kinase inhibitory activity. WO 02/090360 discloses pyrido[2,3-d]pyrimidines useful as kinase enzyme inhibitors and for the treatment of hyperproliferative diseases.

WO 03/000011 discloses phosphorus-containing derivatives of pyrido[2,3-d]pyrimidine as protein kinase inhibitors and for the treatment of bone disorders, cancer and signaling disorders in general.

WO 96/15128 discloses 6-aryl-pyrido[2,3-d]pyrimidines as inhibitors of protein tyrosine kinases and for the treatment of atherosclerosis, restenosis, psoriasis, bacterial infections and cancer.

Despite the progress documented in the above-mentioned literature, there remains a need for new compounds with an improved therapeutic index, such as improved activity, tolerability, selectivity or stability to name only a few.

SUMMARY OF THE INVENTION

The present derivatives are new compounds of the general formula:

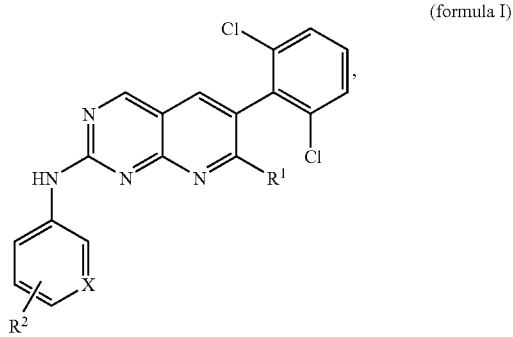

(formula I)

wherein:
$R^1$ is selected from the group consisting of:
(a) —C(O)—NH-alkyl or —C(O)—N(alkyl)$_2$, wherein the alkyl groups of —C(O)—NH-alkyl or —C(O)—N(alkyl)$_2$ are optionally substituted with one or more constituents selected from the group consisting of:
  (1) —OH;
  (2) —NH(alkyl), wherein the alkyl group is optionally substituted with —OH;
  (3) —N(alkyl)$_2$, wherein the alkyl groups are optionally substituted with —OH;
  (4) —NH—C(O)-alkyl, wherein the alkyl group is optionally substituted with —OH;
  (5) —C(O)—NH-alkyl, wherein the alkyl group is optionally substituted with —OH;
  (6) —C(O)—N(alkyl)$_2$, wherein the alkyl groups are optionally substituted with —OH;
  (7) —C(O)—NH$_2$;
  (8) —O-alkyl, wherein the alkyl group is optionally substituted with —OH;
  (9) -heterocyclyl;
  (10) —NH-heterocyclyl;
  (11) —NH—S(O)$_2$-alkyl, wherein the alkyl group is optionally substituted with —OH;
  (12) —S(O)$_2$—NH$_2$; and
  (13) —S(O)-alkyl, wherein the alkyl group is optionally substituted with —OH;
(b) —CN;
(c) —C(O)—NH$_2$;
(d) —C(O)—NH-heterocyclyl;
(e) —C(O)—NH—NH—C(O)—NH$_2$; and
(f) —C(O)—NH—NH—C(O)-alkyl, wherein the alkyl group is optionally substituted with NH(alkyl); or —N(alkyl)$_2$; and $R^2$ is selected from the group consisting of:
(a) halogen;
(b) heterocyclyl;
(c) alkyl, wherein the alkyl group is optionally substituted with one or more constituents selected from the group consisting of:
  (1) —OH;
  (2) —O-alkyl;
  (3) —NH-alkyl; and
  (4) —N(alkyl)$_2$;
(d) —NH—C(O)-alkyl, wherein the alkyl group is optionally substituted with one or more constituents selected from the group consisting of:
  (1) —OH;
  (2) —O-alkyl;
  (3) —NH-alkyl; and
  (4) —N(alkyl)$_2$;
(e) —NH—S(O)$_2$-alkyl, wherein the alkyl group is optionally substituted with one or more constituents selected from the group consisting of:
  (1) —OH;
  (2) —O-alkyl;
  (3) —NH-alkyl; and
  (4) —N(alkyl)$_2$;
(f) —(CH$_2$)$_m$—S(O)$_2$—NH$_2$;
(g) —(CH$_2$)$_m$—S(O)$_2$—N(alkyl)$_2$, wherein the alkyl groups are optionally substituted with one or more constituents selected from the group consisting of:
  (1) —OH;
  (2) —O-alkyl;
  (3) —NH-alkyl; and
  (4) —N(alkyl)$_2$;
(h)-(CH$_2$)$_m$—S(O)$_2$—NH-(alkyl), wherein the alkyl group is optionally substituted with one or more constituents selected from the group consisting of:
  (1) —OH;
  (2) —O-alkyl;
  (3) —NH-alkyl; and
  (4) —N(alkyl)$_2$;

(i) —O-alkyl, wherein the alkyl group is optionally substituted with one or more constituents selected from the group consisting of:
  (1) —OH;
  (2) —O-alkyl;
  (3) —NH-alkyl; and
  (4) —N(alkyl)$_2$; and
(j) —S(O)$_n$-alkyl, wherein the alkyl group is optionally substituted with one or more constituents selected from the group consisting of:
  (1) —OH;
  (2) —O-alkyl;
  (3) —NH-alkyl; and
  (4) —N(alkyl)$_2$;
X is —CH= or —N=;
m is 0, 1, 2, 3, 4, 5 or 6;
n is 0, 1 or 2;

and pharmaceutically acceptable salts or esters thereof.

The compounds of formula I are useful for preventing or treating a disease mediated by tyrosine kinase such as cancer; inflammatory or immunological diseases; central nervous system diseases; bone diseases, and benign hyperplasia.

The compounds according to this invention show activity as protein kinase inhibitors, in particular src family tyrosine kinase inhibitors, and may therefore be useful for the treatment of diseases mediated by said tyrosine kinases. The family of tyrosine kinases plays an important role in the regulation of cell signaling and cell proliferation by phosphorylating tyrosine residues of peptides and proteins. Inappropriate activation of tyrosine kinases is known to be involved in a variety of disease states including inflammatory, immunological, CNS disorders, or oncological disorders, or bone diseases. See for example Susva, M., et al., Trends Pharmacol. Sci. 21 (2000) 489–495; Biscardi, J. S., et al., Adv. Cancer Res. 76 (2000) 61–119.

Compounds of the present invention may be used as active agents in the prevention and therapy of, for example, transplant rejection, inflammatory bowel syndrome, rheumatoid arthritis, psoriasis, restenosis, allergic asthma, Alzheimer's disease, Parkinson, stroke, osteoporosis, cancer, and benign hyperplasias. In particular embodiments, the compounds are especially useful in the treatment or control of cancer.

The compounds of the present invention have surprisingly been found to show improved metabolic stability and/or selectivity, together with at least the same activity against src-tyrosine kinase compared to compounds known in the art.

The present invention relates to the compounds of formula I and pharmaceutically acceptable salts or esters and their enantiomeric forms, the preparation of the above-mentioned compounds, compositions containing them and their manufacture as well as the use of the above-mentioned compounds in the control or prevention of illnesses, especially of illnesses and disorders as mentioned above or in the manufacture of corresponding pharmaceutical compositions.

DETAILED DESCRIPTION OF THE INVENTION

As used herein, the term "alkyl" means a saturated, straight-chain or branched-chain hydrocarbon containing from 1 to 6, preferably from 1 to 4, carbon atoms, such as methyl, ethyl, n-propyl, isopropyl, n-butyl, 2-butyl, t-butyl, n-pentyl, n-hexyl as well as their isomers. "Optionally substituted" alkyl groups are alkyl groups as defined above, which are either unsubstituted or one or more times substituted; preferably unsubstituted or one or two times substituted. As used herein, the term "(C$_1$–C$_4$) alkyl" means a saturated, straight-chain or branched-chain hydrocarbon containing from 1 to 4 carbon atoms, such as methyl, ethyl, n-propyl, isopropyl, n-butyl, 2-butyl, or t-butyl.

As used herein, the term halogen means fluorine, chlorine, bromine or iodine, preferably fluorine, chlorine or bromine and more preferably fluorine or chlorine.

The term "heterocyclyl" as used herein means a 5 to 10 membered, mono- or bicyclic, aromatic or non-aromatic hydrocarbon, wherein 1 to 3, preferably 1 or 2, carbon atoms are replaced by a nitrogen-, oxygen- or sulfur atom, or by a group —S(O)$_2$—. Said heterocyclyl group is optionally substituted once or several times with alkyl, oxo or —C(O)—NH$_2$. Examples are 2-oxo-imidazolidin-1-yl; pyrrolidin-2-yl; pyrrolidin-3-yl; 2-oxo-pyrrolidin-1-yl; 1-methyl-pyrrolidin-2-yl; imidazol-4-yl; pyrazol-3-yl; 2-methyl-pyrazol-3-yl; 1-methyl-pyrazol-5-yl; 1,5-dimethyl-pyrazol-3-yl; 4-carbamoyl-pyrazol-3-yl; piperidin-3-yl; piperidin-4-yl; 1-methyl-piperidin-4-yl; morpholin-4-yl; pyridin-2-yl; 1-aza-bicyclo [2.2.2]oct-3-yl or 4,4-dioxo-2,3-dihydro-benzo[1,4]oxathiine-6-yl.

Preferably the substituent R$^2$ in formula I is located in para or meta position.

The term "a therapeutically effective amount" of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

A preferred embodiment of the present invention are the compounds of formula I, wherein X is —CH=;
R$^1$ is —C(O)—NH-alkyl, wherein the alkyl group is optionally substituted with one or more constituents selected from the group consisting of:
  (a) —OH;
  (b) —NH(alkyl), wherein the alkyl group is optionally substituted with —OH
  (c) —N(alkyl)$_2$, wherein the alkyl groups are optionally substituted with —OH
  (d) —NH—C(O)-alkyl, wherein the alkyl group is optionally substituted with —OH
  (e) —C(O)—NH-alkyl, wherein the alkyl group is optionally substituted with —OH
  (f) —C(O)—N(alkyl)$_2$, wherein the alkyl groups are optionally substituted with —OH (g) —C(O)—NH$_2$;
(h) —O-alkyl, wherein the alkyl group is optionally substituted with —OH
(i) -heterocyclyl;
(j) —NH-heterocyclyl;
(k) —NH—S(O)$_2$-alkyl, wherein the alkyl group is optionally substituted with —OH
(l) —S(O)$_2$—NH$_2$; and
(m) —S(O)-alkyl, wherein the alkyl group is optionally substituted with —OH; and R$^2$ has the significance given above.

Another embodiment of the present invention are the compounds of formula I, wherein
X is —CH=;
R$^1$ is —C(O)—NH-methyl; or
—C(O)—NH-ethyl,
wherein the methyl or ethyl group is unsubstituted or once substituted with a constituent selected from the group consisting of:
(a) —OH;
(b) -pyrrolidinyl; and
(c) —NH—S(O)$_2$—CH$_3$; and R$^2$ has the significance given above.

Still another embodiment of the present invention are the compounds of formula I, wherein
X is —CH=;
R$^1$ is —C(O)—NH-ethyl or —C(O)—NH-methyl, wherein the ethyl or methyl groups are once substituted with a constituent selected from the group consisting of:
(a) —OH; and
(b) -pyrrolidinyl; and R$^2$ is selected from the group consisting of:
(a) morpholin-4-yl;
(b) —NH—S(O)$_2$—CH$_3$;
(c) —O-alkyl, wherein the alkyl group is optionally once substituted with a constituent selected from the group consisting of:
(1) —OH;
(2) —O-alkyl;
(3) —NH-alkyl; and
(4) —N(alkyl)$_2$; and
(d) —S(O)$_n$-alkyl, wherein the alkyl group is optionally once substituted with a constituent selected from the group consisting of:
(1) —OH;
(2) —O-alkyl;
(3) —NH-alkyl; and
(4) —N(alkyl)$_2$;

n is 0, 1 or 2; and pharmaceutically acceptable salts or esters thereof.

Such compounds are for example:
6-(2,6-Dichloro-phenyl)-2-[4-(2-hydroxy-ethoxy)-phenylamino]-pyrido[2,3-d]pyrimidine-7-carboxylic acid (2-hydroxy-ethyl)-amide;
6-(2,6-Dichloro-phenyl)-2-(4-morpholin-4-yl-phenylamino)-pyrido[2,3-d]pyrimidine-7-carboxylic acid (2-hydroxy-ethyl)-amide;
6-(2,6-Dichloro-phenyl)-2-[4-(2-hydroxy-ethoxy)-phenylamino]-pyrido[2,3-d]pyrimidine-7-carboxylic acid ((R)-1-pyrrolidin-2-ylmethyl)-amide; or
6-(2,6-Dichloro-phenyl)-2-(4-morpholin-4-yl-phenylamino)-pyrido[2,3-d]pyrimidine-7-carboxylic acid ((R)-1-pyrrolidin-2-ylmethyl)-amide.

Yet another embodiment of the present invention are the compounds of formula I, wherein
X is —CH=;
R$^1$ is —C(O)—NH—(CH$_2$)$_2$—NH—S(O)$_2$—CH$_3$;
R$^2$ is selected from the group consisting of:
(a) morpholin-4-yl;
(b) 4-methyl-piperazin-1-yl;
(c) —NH—S(O)$_2$—CH$_3$;
(d) —O-alkyl, wherein the alkyl group is optionally once substituted with a constituent selected from the group consisting of:
(1) —OH;
(2) —O-alkyl;
(3) —NH-alkyl; and
(4) —N(alkyl)$_2$; and
(e) —S(O)$_n$-alkyl, wherein the alkyl group is optionally once substituted with a constituent selected from the group consisting of:
(1) —OH;
(2) —O-alkyl;
(3) —NH-alkyl; and
(4) —N(alkyl)$_2$;

n is 0, 1 or 2; and pharmaceutically acceptable salts or esters thereof.

Such compounds are for example:
6-(2,6-Dichloro-phenyl)-2-(4-morpholin-4-yl-phenylamino)-pyrido[2,3-d]pyrimidine-7-carboxylic acid (2-methanesulfonylamino-ethyl)-amide;
6-(2,6-Dichloro-phenyl)-2-[4-(2-hydroxy-ethoxy)-phenylamino]-pyrido[2,3-d]pyrimidine-7-carboxylic acid (2-methanesulfonylamino-ethyl)-amide;
6-(2,6-Dichloro-phenyl)-2-(3-methanesulfonylamino-phenylamino)-pyrido[2,3-d]pyrimidine-7-carboxylic acid (2-methanesulfonylamino-ethyl)-amide;
6-(2,6-Dichloro-phenyl)-2-[3-(2-hydroxy-ethylsulfanyl)-phenylamino]-pyrido[2,3-d]pyrimidine-7-carboxylic acid (2-methanesulfonylamino-ethyl)-amide;
6-(2,6-Dichloro-phenyl)-2-[4-(4-methyl-piperazin-1-yl)-phenylamino]-pyrido[2,3-d]pyrimidine-7-carboxylic acid (2-methanesulfonylamino-ethyl)-amide; or
6-(2,6-Dichloro-phenyl)-2-(3-methylsulfanyl-phenylamino)-pyrido[2,3-d]pyrimidine-7-carboxylic acid (2-methanesulfonylamino-ethyl)-amide.

Yet another embodiment of the present invention are the compounds of formula I, wherein
X is —CH=;
R$^1$ is —C(O)—NH$_2$; and
R$^2$ is selected from the group consisting of:
(a) morpholin-4-yl;
(b) —NH—S(O)$_2$—CH$_3$;
(c) —O-alkyl; wherein the alkyl group is optionally once substituted with a constituent selected from the group consisting of:
(1) —OH;
(2) —O-alkyl;
(3) —NH-alkyl; or
(4) —N(alkyl)$_2$; and
(d) —S(O)$_n$-alkyl, wherein the alkyl group is optionally once substituted with a constituent selected from the group consisting of:
(1) —OH;
(2) —O-alkyl;
(3) —NH-alkyl; or
(4) —N(alkyl)$_2$;

n is 0, 1 or 2; and pharmaceutically acceptable salts or esters thereof.

Such compounds are for example:
6-(2,6-Dichloro-phenyl)-2-(4-morpholin-4-yl-phenylamino)-pyrido[2,3-d]pyrimidine-7-carboxylic acid amide; or
6-(2,6-Dichloro-phenyl)-2-[4-(2-hydroxy-ethoxy)-phenylamino]-pyrido[2,3-d]pyrimidine-7-carboxylic acid amide.

Yet another embodiment of the present invention are the compounds of formula I, wherein
X is —CH═;
$R^1$ is —CN; and
$R^2$ is selected from the group consisting of:
(a) morpholin-4-yl;
(b) —NH—S(O)$_2$—CH$_3$;
(c) —O-alkyl, wherein the alkyl group is optionally once substituted with a constituent selected from the group consisting of:
(1) —OH;
(2) —O-alkyl;
(3) —NH-alkyl; and
(4) —N(alkyl)$_2$; and
(d) —S(O)$_n$-alkyl, wherein the alkyl group is optionally once substituted with a constituent selected from the group consisting of:
(1) —OH;
(2) —O-alkyl;
(3) —NH-alkyl; and
(4) —N(alkyl)$_2$;
n is 0, 1 or 2; and pharmaceutically acceptable salts or esters thereof.
Such compounds are for example:
6-(2,6-Dichloro-phenyl)-2-[4-(2-diethylamino-ethoxy)-phenylamino]-pyrido[2,3-d]pyrimidine-7-carbonitrile;
6-(2,6-Dichloro-phenyl)-2-(4-morpholin-4-yl-phenylamino)-pyrido[2,3-d]pyrimidine-7-carbonitrile; or
6-(2,6-Dichloro-phenyl)-2-[4-(2-hydroxy-ethoxy)-phenylamino]-pyrido[2,3-d]pyrimidine-7-carbonitrile.

Yet another embodiment of the present invention are the compounds of formula I, wherein
X is —N═;
$R^1$ is —C(O)—NH—(CH$_2$)$_2$—NH—S(O)$_2$—CH$_3$; and
$R^2$ is selected from the group consisting of:
(a) alkyl, wherein the alkyl group is optionally once substituted with a constituent selected from the group consisting of:
(1) —OH;
(2) —O-alkyl;
(3) —NH-alkyl; and
(4) —N(alkyl)$_2$;
(b) —NH—S(O)$_2$—CH$_3$;
(c) —O-alkyl, wherein the alkyl group is optionally once substituted with a constituent selected from the group consisting of:
(1) —OH;
(2) —O-alkyl;
(3) —NH-alkyl; and
(4) —N(alkyl)$_2$;
(d) —S(O)$_n$-alkyl, wherein the alkyl group is optionally once substituted with a constituent selected from the group consisting of:
(1) —OH;
(2) —O-alkyl;
(3) —NH-alkyl; and
(4) —N(alkyl)$_2$;
n is 0, 1 or 2; and pharmaceutically acceptable salts or esters thereof.

Such compounds are for example:
6-(2,6-Dichloro-phenyl)-2-(6-methyl-pyridin-3-ylamino)-pyrido[2,3-d]pyrimidine-7-carboxylic acid (2-methane-sulfonylamino-ethyl)-amide.

Still another embodiment of the invention is a process for the manufacture of the compounds according to this invention, wherein
(a) the sulfide group in the compounds of the general formula (II)

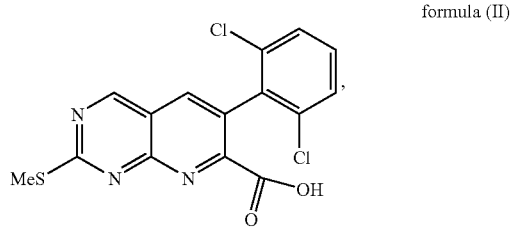

formula (II)

is converted into the corresponding sulfoxide group, which sulfoxide group is
(b) substituted by the respective anilines of formula (II-A)

formula (II-A)

wherein $R^2$ and X have the meanings given herein before, to give the compounds of the general formula (IV)

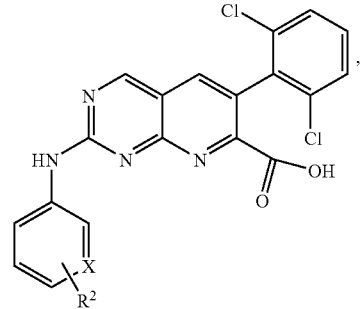

formula (IV)

(c) the —COOH group in formula (IV) is converted into an amide derivative of formula (I); and
(d) if desired a primary amide derivative obtained from (c) is further converted into its corresponding 7-carbonitril derivative of formula (I); and
(e) if desired said compound of the general formula (I), obtained from (c) or (d), is converted into a pharmaceutically acceptable salt or ester.

In a more detailed description, the compounds of formula (I) wherein $R^1$ is attached via an amide group are represented by the general formula (Ia). Such compounds can be pre pared from the carboxylic acids of formula (II), using standard reactions well known to one skilled in the art. The synthesis of the compounds of the general formula (Ia) is shown in scheme 1, wherein $R^3$ has the significance given above for $R^1$ without the group —CN, therefore $R^3$ is selected from the group consisting of:
(a) —C(O)—NH-alkyl or —C(O)—N(alkyl)$_2$, wherein the alkyl groups of —C(O)—NH-alkyl or —C(O)—N(alkyl)$_2$ are optionally substituted with one or more constituents selected from the group consisting of:
  (1) —OH;
  (2) —NH(alkyl), wherein the alkyl group is optionally substituted with —OH;
  (3) —N(alkyl)$_2$, wherein the alkyl groups are optionally substituted with —OH;
  (4) —NH—C(O)-alkyl, wherein the alkyl group is optionally substituted with —OH;
  (5) —C(O)—NH-alkyl, wherein the alkyl group is optionally substituted with —OH;
  (6) —C(O)—N(alkyl)$_2$, wherein the alkyl groups are optionally substituted with —OH;
  (7) —C(O)—NH$_2$;
  (8) —O-alkyl, wherein the alkyl group is optionally substituted with —OH;
  (9) -heterocyclyl;
  (10) —NH-heterocyclyl;
  (11) —NH—S(O)$_2$-alkyl, wherein the alkyl group is optionally substituted with —OH;
  (12) —S(O)$_2$—NH$_2$; and
  (13) —S(O)-alkyl, wherein the alkyl group is optionally substituted with —OH;
(b) —C(O)—NH$_2$;
(c) —C(O)—NH-heterocyclyl;
(d) —C(O)—NH—NH—C(O)—NH$_2$; or
(e) —C(O)—NH—NH—C(O)-alkyl, wherein the alkyl group is optionally substituted with —NH(alkyl) or —N(alkyl)$_2$;

and $R^2$ and X have the significances given above.

The derivatives of the general formula (I), or a pharmaceutically acceptable salt or ester thereof, may be prepared by any process known to be applicable for the preparation of chemically-related compounds by the one skilled in the art. Such processes, when used to prepare the diazine derivatives of formula (I), or a pharmaceutically-acceptable salt thereof, are provided as a further feature of the invention and are illustrated by the following representative examples of scheme 1 to scheme 4, in which, unless otherwise stated, $R^1$, $R^2$ and X have the significance given herein before. Necessary starting materials are commercially available or may be obtained by standard procedures of organic chemistry. The preparation of such starting materials is described within the accompanying examples. Alternatively necessary starting materials are obtainable by analogous procedures to those illustrated which are within the ordinary skill of an organic chemist.

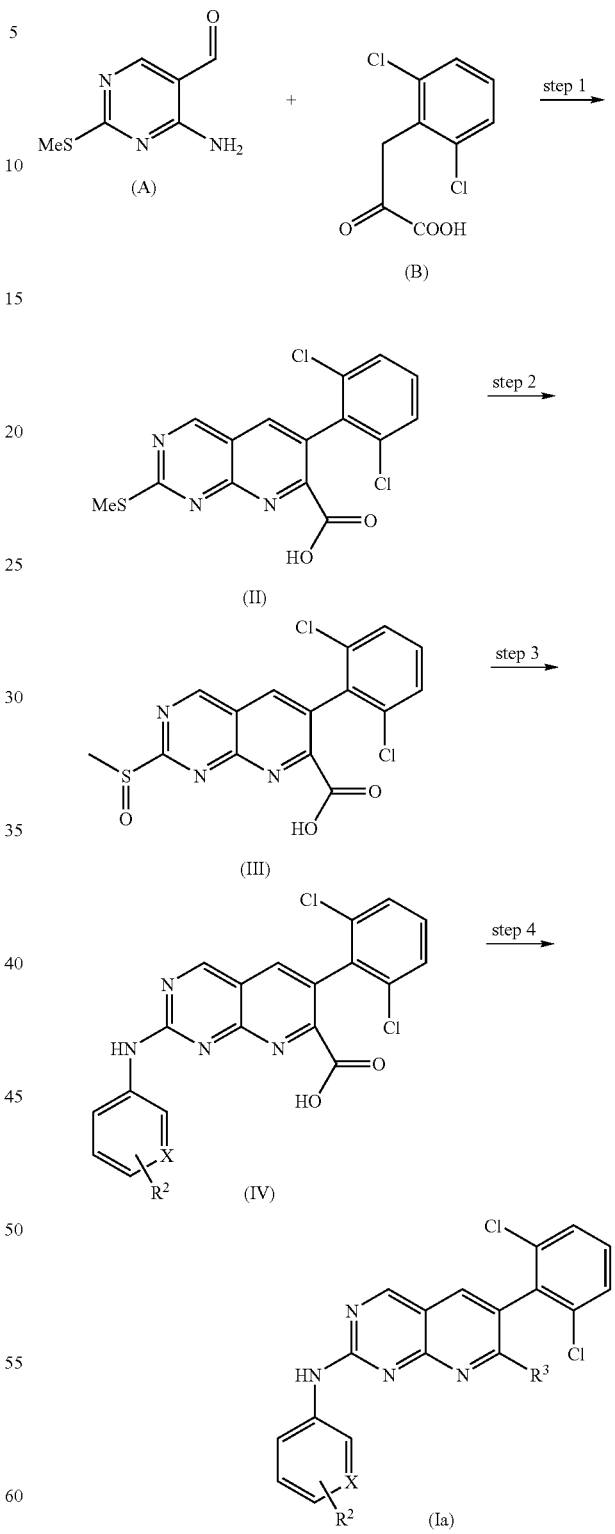

Alternatively, the carboxylic acids (II) can first be converted to carboxamides (V) and subsequently substituted by anilines on position 2 according to scheme 2, wherein $R^3$, $R^2$ and X have the significances given above.

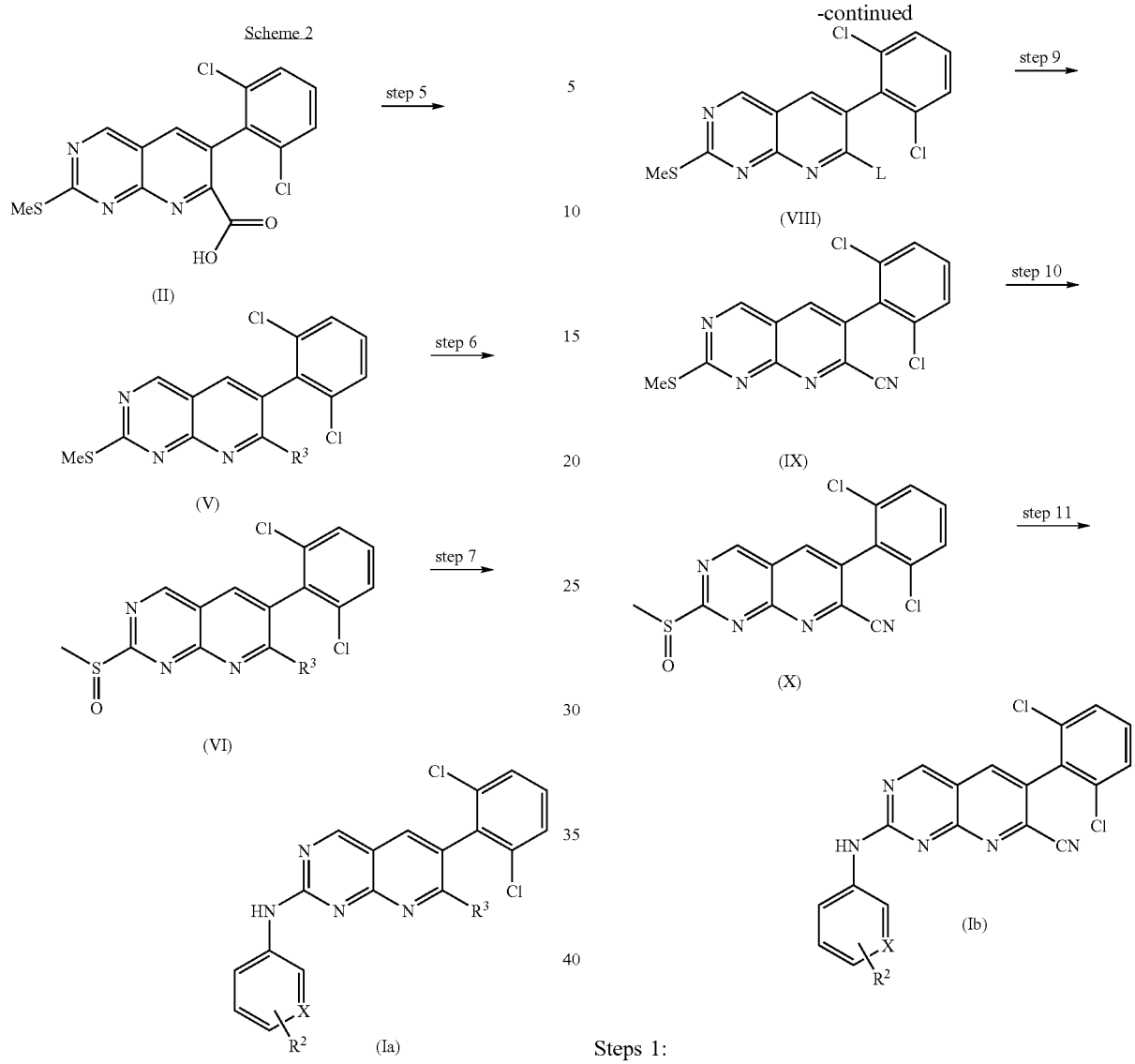

Primary carboxamides of the formulae (Ia) or (V), wherein R³ is —C(O)—NH₂, can be converted into nitriles of the general formula (Ib) by conventional methods, e.g. dehydration with SOCl₂ or POCl₃. Said nitriles of formula (Ib) may also be prepared from known pyridine derivatives (VII) according to scheme 3, wherein R² and X have the significances given herein before and L is a suitable leaving group.

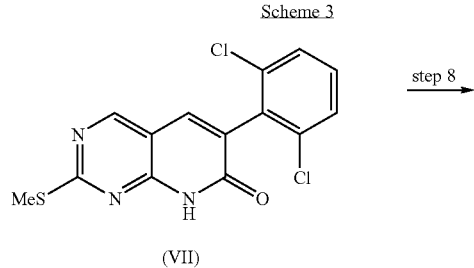

Steps 1:
3-(2,6-dichloro-phenyl)-pyruvic acid of formula (B), or in general arylpyruvic acids, can be condensed with a suitable pyrimidine carbaldehyde of formula (A) to give compound (II). Said condensation reaction can be performed under basic conditions, e.g. with sodium hydroxide (NaOH) in water or methanol (MeOH) or 1,8-Diazabicyclo[5.4.0]undec-7-ene (DBU) or potassium tert-butoxide (KOtBu) in dimethyl formamide (DMF), 1-Methyl-2-pyrrolidinone (NMP) or tetrahydrofuran (THF). Alternatively, the condensation reaction is performed in acetic acid in the presence of sodium acetate. Reaction temperatures range from room temperature (RT) to 150° C.

Steps 2, 6 and 10:
A methylthio or alternatively any other alkylthio or arylthio group on position 2 of the pyridopyrimidines of formulae (II), (V) or (IX) can be converted into a suitable leaving group by oxidation to the corresponding sulfone or sulfoxide of the formulae (III), (VI) or (X). Suitable reagents are for instance 3-Chloroperoxybenzoic acid (mCPBA) or 2-benzenesulfonyl-3-phenyl-oxaziridine in inert solvents like dichloromethane (CH₂Cl₂, chloroform (CHCl₃), or MTBE at temperatures ranging from −40° C. to +65° C. As used herein, MTBE refers to Methyl tert-butyl ether.

Steps 3, 7, and 11:

The sulfoxides or sulfones from steps 2, 6 or 10 can be reacted in purified form or as crude products with anilines to give 2-anilino substituted pyridopyrimidines of the formulae (IV), (Ia, scheme 2) or (Ib). The reaction may be performed in excess aniline as the solvent or in an inert solvent like $CH_2Cl_2$, toluene, acetonitrile, dimethyl formamide (DMF), dimethyl sulfoxide (DMSO) or 1-Methyl-2-pyrrolidinone (NMP), and at temperatures in the range from 0° C. to 150° C. Acids like trifluoroacetic acid (TFA) or hydrochloric acid (HCl) may be added to catalyze the reaction. If mCPBA has been used for the previous oxidation step, the formed m-chlorobenzoic acid present in the crude reaction mixture may serve as the catalyst.

Steps 4 and 5:

The appropriate carboxylic acids of formulae (IV) or (II, scheme 2) can be converted into amide derivatives of the formulae (Ia, scheme 1) or (V) by standard procedures known in the art. For instance, the acid is first activated by reaction with a carbodiimide or carbonyl diimidazole or oxalyl chloride, and subsequently reacted without isolation with the appropriate substituted amine or ammonia. This reaction is best performed in an inert solvent like THF, $CH_2Cl_2$ or NMP at temperatures ranging from 0° C. to 150° C.

Step 8:

A suitable leaving group "L" in (VIII) may be a triflate, which can be prepared from (VII) by reaction with trifluoromethanesulfonic anhydride ($Tf_2O$) or N-phenyltrifluoromethanesulfonimide [$PhN(Tf)_2$] in an inert solvent like THF or $CH_2Cl_2$ or NMP, in the presence of a base like triethyl amine ($NEt_3$) pyridine, potassium tert-butoxide (KOtBu), lithium diisopropylamide (LDA), NaH, or $K_2CO_3$. Another leaving group is a chlorine or bromine atom which can be introduced by halogenation of the pyridone with $POCl_3$ or $POBr_3$.

Step 9:

The leaving group "L" in (VIII) can be substituted by an inorganic cyanide like potassium cyanide (KCN), sodium cyanide (NaCN) or copper cyanide (CuCN) in an inert solvent like diglyme, DMF, NMP, or sulfolane at temperatures from RT to 180° C., to give (IX). Preferably, this reaction can also be catalyzed by a transition metal catalyst, e.g. a Pd- or Ni catalyst. In this case, also zinc cyanide ($Zn(CN)_2$) may be applied as the cyanide source.

Certain side chains in $R^3$ or $R^2$ may require protection during the reaction sequences. Here standard protection and deprotection procedures being well known in the art may be applied. For instance, primary and secondary amines can be applied in t-butoxycarbonyl (Boc) or benzyloxycarbonyl protected form and the protecting group can be removed as a last reaction step by treatment with an acid like HCl or TFA.

The compounds of the general formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-tartaric acid, mandelic acid, malic acid, lactic acid, or camphorsulfonic acid. Alternatively separation of the enantiomers can also be achieved by using chromatography on chiral HPLC-phases which are commercially available.

The compounds according to the present invention may exist in the form of their pharmaceutically acceptable salts or esters. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethylammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin, R. J. et al, Organic Proc. Res. Dev. 4 (2000) 427–435.

The compounds according to this invention and their pharmaceutically acceptable salts or esters can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

A pharmaceutical preparation was obtained by using the following procedure:

1. Weigh 4.0 g glass beads in custom made tube 25% Glass filled Polytetrafluoroethylene (PTFE) (=GL 25), 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).

7. Extract suspension from beads with two layers of filter (100 μm) on a filter holder, coupled to a recipient vial by centrifugation at 400 g for 2 min.
8. Move extract to measuring cylinder.
9. Repeat washing with small volumes (here 1 ml steps) until final volume is reached or extract is clear.
10. Fill up to final volume with gelatin and homogenise.

The above described preparation yields micro-suspensions of the compounds of formula I with particle sizes between 1 and 10 μm. The suspensions are suitable for oral applications and were used in the in vivo pharmacokinetic testings described below.

The activity of the compounds according to this invention as inhibitors for the src-family tyrosine kinases was shown by using the following assay. As used herein Ro refers to the peptide: $NH_2$-A-E-E-E-I-Y-G-E-F-E-A-K-K-K-K-$CONH_2$ (SEQ ID NO: 1); Ja133-Ro refers to the peptide: Ja133-G-Aminocaprylic acid-A-E-E-E-I-Y-G-E-F-E-A-K-K-K-K-$CONH_2$(SEQ ID NO: 2), wherein Ja133 is LightCycler-Red 640-N-hydroxy succinimide ester; PT66 refers to a phosphotyrosine specific antibody which can detect the phoyphorylated tyrosine of protein tyrosine kinase; and TCEP refers to Tris(2-carboxyethyl)phosphine; Lck Cisbio Mab PT66-K refers to Anti-Phosphotyrosine (PT66)-Cryptate; and Src EG&G Wallac PT66 Eu-W1024 refers to $Eu^{3+}$-labelled Anti-Phosphotyrosine (PT66)-Cryptate.

SRC-Inhibitor-Assay Parameters:

Reaction mixture:

| | |
|---|---|
| ATP | 5 μM |
| Peptide (Ro + Ja133-Ro) | 10 μM |
| Ja133-Ro | 196 nM |
| Ro | 9.8 μM |
| PT66 | 230 ng/ml |
| Assay buffer: | 4 mM $MgCl_2$ |
| | 2 mM TCEP |
| | 50 mM HEPES |
| | 0.1% Tween 20 |
| | pH 7.3 |
| Enzyme: | 2.5 U/ml |
| Inhibitor: | max. 25 μM |
| | min. 0.42 nM |
| Material: | |
| Eu-labelled phosphotyrosine antibody: | for Lck Cisbio Mab PT66-K, for Src EG&G Wallac PT66 Eu-W1024 (all commercially available). |
| Peptides: Ro: | $NH_2$-A-E-E-E-I-Y-G-E-F-E-A-K-K-K-K-$CONH_2$ (SEQ ID NO: 1), and |
| Ja133-Ro: | Ja133-G-Aminocaprylic acid-A-E-E-E-I-Y-G-E-F-E-A-K-K-K-K-$CONH_2$ (SEQ ID NO: 2), wherein Ja133 is LightCycler-Red 640-N-hydroxy succinimide ester; | whereby both peptides were synthesized by an optimized solid phase peptide synthesis protocol (Merrifield, Fed. Proc. Fed. Amer. Soc. Exp. Biol. 21(1962) 412) on a Zinsser SMP350 peptide synthesizer. Shortly, the peptide was assembled on 160 mg (22.8 μmol scale) of a Rink-Linker modified polystyrene solid phase by repeatedly conjugating an twenty fold excess of amino acids each protected by temporary piperidine labile Fmoc- and permanent acid labile tert-Bu-, BOC- and tert-BuO-groups depending on the side chain function. The substrate sequence AEEE-IYGEFEAKKKK (SEQ ID NO: 1) was N-terminal additionally mounted with the spacer amino acids Aminocaprylic acid and Glycin. After cleavage of the N-terminal temporary protecting group the still attached and protected peptide was labeled with a 1.5 fold amount of LightCycler-Red 640-N-hydroxy succinimide ester (purchased by Roche Diagnostics GmbH) and triethylamine. After 3 hrs. the resin was washed with Dimethylformamide and Isopropanol until the eluates of the blue resin got colorless. The fully protected and labeled peptide was removed from the solid phase and released from the permanent protecting groups by treatment with a mixture of 80% trifluoroacetic acid, 10% Ethanedithiol, 5% Thioanisol and 5% Water. The substrate was finally isolated by a preparative reverse phase HPLC purification. The purification yielded 12.2 mg RP-HPLC single peak pure blue material (lyophilisate). The identity was proven by Matrix Assisted Laser Desorption Ionization (MALDI) mass spectroscopy [2720.0].

Enzymes: Upstate Lck ($p56^{lck}$, active), Upstate Src ($p60^{c-src}$, partially purified) were purchased from Upstate Biotechnology, Inc., Lake Placid, N.Y. (UBI).

Time-resolved Fluorescence Assay: Reader: Perkin Elmer, Wallac Viktor 1420-040 multilabel counter; Liquid handling system: Beckman Coulter, Biomek 2000.

ATP, Tween 20, HEPES were purchased from Roche Molecular Biochemicals, $MgCl_2$ and $MnCl_2$ were purchased from Merck Eurolab, TCEP was purchased from Pierce, 384 Well low volume fluorescence plates was purchased from Falcon.

Assay Description:

At first the enzyme is pre-incubated for 15 min. at 15° C. in aqueous solution with corresponding amounts of inhibitors according to this invention. Then the phosphorylation reaction is started by adding a reaction mixture, containing ATP, Peptide and PT66, and subsequent shaking. The proceeding of this reaction is immediately monitored using time resolved fluorescence spectroscopy in a suitable well plate reader.

The $IC_{50}$-values can be obtained from the reaction rates by using a non-linear curve fit (EXCELFIT software, from ID Business Solution Ltd., Guilford, Surrey, UK).

| Ex-No. | Compound-Name | $IC_{50}$ src [μM] | $IC_{50}$ lck [μM] |
|---|---|---|---|
| 7-1 | 6-(2,6-Dichloro-phenyl)-2-[4-(2-diethylamino-ethoxy)-phenylamino]-pyrido[2,3-d]pyrimidine-7-carbonitrile | 0.0005 | 0.0027 |
| 7-2 | 6-(2,6-Dichloro-phenyl)-2-(4-morpholin-4-yl-phenylamino)-pyrido[2,3-d]pyrimidine-7-carbonitrile | 0.0013 | 0.0117 |
| 4 | 6-(2,6-Dichloro-phenyl)-2-[4-(2-hydroxy-ethoxy)-phenylamino]-pyrido[2,3-d]pyrimidine-7-carbonitrile | 0.0017 | 0.0064 |

-continued

| Ex-No. | Compound-Name | IC$_{50}$ src [μM] | IC$_{50}$ lck [μM] |
|---|---|---|---|
| 8-1 | 6-(2,6-Dichloro-phenyl)-2-(4-morpholin-4-yl-phenylamino)-pyrido[2,3-d]pyrimidine-7-carboxylic acid amide | 0.0010 | 0.0037 |
| 5 | 6-(2,6-Dichloro-phenyl)-2-[4-(2-hydroxy-ethoxy)-phenylamino]-pyrido[2,3-d]pyrimidine-7-carboxylic acid amide | 0.0022 | 0.0076 |
| 6-1 | 6-(2,6-Dichloro-phenyl)-2-[4-(2-hydroxy-ethoxy)-phenylamino]-pyrido[2,3-d]pyrimidine-7-carboxylic acid (2-hydroxy-ethyl)-amide | 0.0054 | 0.0082 |
| 6-2 | 6-(2,6-Dichloro-phenyl)-2-(4-morpholin-4-yl-phenylamino)-pyrido[2,3-d]pyrimidine-7-carboxylic acid (2-hydroxy-ethyl)-amide | 0.0018 | 0.0041 |
| 6-3 | 6-(2,6-Dichloro-phenyl)-2-(4-morpholin-4-yl-phenylamino)-pyrido[2,3-d]pyrimidine-7-carboxylic acid (2-methanesulfonylamino-ethyl)-amide | 0.0009 | 0.0015 |
| 6-4 | 6-(2,6-Dichloro-phenyl)-2-[4-(2-hydroxy-ethoxy)-phenylamino]-pyrido[2,3-d]pyrimidine-7-carboxylic acid (2-methanesulfonylamino-ethyl)-amide | 0.0011 | 0.0016 |
| 6-5 | 6-(2,6-Dichloro-phenyl)-2-[4-(2-hydroxy-ethoxy)-phenylamino]-pyrido[2,3-d]pyrimidine-7-carboxylic acid ((R)-1-pyrrolidin-2-ylmethyl)-amide | 0.0006 | 0.0017 |
| 1 | 6-(2,6-Dichloro-phenyl)-2-(4-morpholin-4-yl-phenylamino)-pyrido[2,3-d]pyrimidine-7-carboxylic acid ((R)-1-pyrrolidin-2-ylmethyl)-amide | 0.0004 | 0.0017 |
| 6-6 | 6-(2,6-Dichloro-phenyl)-2-(3-methanesulfonylamino-phenylamino)-pyrido[2,3-d]pyrimidine-7-carboxylic acid (2-methanesulfonylamino-ethyl)-amide | 0.0002 | 0.0013 |
| 3 | 6-(2,6-Dichloro-phenyl)-2-[3-(2-hydroxy-ethylsulfanyl)-phenylamino]-pyrido[2,3-d]pyrimidine-7-carboxylic acid (2-methanesulfonylamino-ethyl)-amide | 0.0007 | 0.0020 |
| 2 | 6-(2,6-Dichloro-phenyl)-2-[4-(4-methyl-piperazin-1-yl)-phenylamino]-pyrido[2,3-d]pyrimidine-7-carboxylic acid (2-methanesulfonylamino-ethyl)-amide | 0.0003 | 0.0010 |
| 6-7 | 6-(2,6-Dichloro-phenyl)-2-(3-methylsulfanyl-phenylamino)-pyrido[2,3-d]pyrimidine-7-carboxylic acid (2-methanesulfonylamino-ethyl)-amide | 0.0025 | 0.0099 |
| 6-8 | 6-(2,6-Dichloro-phenyl)-2-(6-methyl-pyridin-3-ylamino)-pyrido[2,3-d]pyrimidine-7-carboxylic acid (2-methanesulfonylamino-ethyl)-amide | 0.0047 | 0.0078 |

In Vivo Assay on Tumor Inhibition:

To generate primary tumors, HT-29 colon carcinoma cells ($2.5 \times 10^6$ in a volume of 100 μl) are injected subcutaneously into the left flank of female Severe Combined Immunodeficient (SCID) mice using a 1 ml syringe and a 26G needle. The HT-29 cells have been originally obtained from the NCI and deposited in a working cell bank. The cells are thawed and expanded in vitro before use in the experiment. Mice are assigned to the treatment groups on day 9. For grouping (n=12 mice per group), the animals are randomized to get a similar mean primary tumor volume of ca. 120 mm$^3$ per group. The test compounds are administered orally once per day as a suspension in 7.5% gelatine 0.22% NaCl with an administration volume of 10 ml/kg based on actual body weights. Treatment is initiated on day 10, and carried out until day 30, the final day of the study. The subcutaneous primary tumors are measured twice weekly, starting on day 7 after tumor cell implantation, in two dimensions (length and width) using an electronic caliper. The volume of the primary tumor is calculated using the formula: V[mm$^3$]= (length [mm]×width [mm]×width [mm])/2. In addition, the body weight of all animals is recorded at least twice weekly. Finally, at the end of the study the tumors are explanted and weighed.

The following examples, references are provided to aid the understanding of the present invention, the true scope of which is set forth in the appended claims. It is understood that modifications can be made in the procedures set forth without departing from the spirit of the invention.

Starting Materials a) Ethyl 3-(2,6-dichlorophenyl)-2-oxopropionate 12.4 g magnesium powder were activated by dry stirring for 1 hr under Ar atmosphere. 250 ml dry ether were added. 25 g 2,6-dichlorobenzyl bromide were dissolved in 150 ml ether and 10 ml of this solution were added to the stirred magnesium suspension. A small amount of iodine was added and the mixture warmed gently for 10 min to start the reaction. Then the remainder of the 2,6-dichlorobenzyl bromide solution was added at room temperature (RT) in 1 hr and the mixture was subsequently refluxed for 2 hrs, whereupon a solution is formed.

Then this solution was cooled to −30° C. and added quickly to a solution of 29.5 g diethyl oxalate in 150 ml ether, which has been pre-cooled to −50° C. The mixture was allowed to reach RT and stirring at RT was continued for another 14 hrs.

The mixture was washed with aqueous HCl, dried and concentrated under vacuum. 1 first crop of 8.1 g of crystalline title product was isolated by filtration. A second crop of 8.7 g was obtained after evaporation of all volatiles at 70° C./20 mbar.

b) 3-(2,6-dichlorophenyl)-2-oxopropionic acid 8.1 g of the above ethyl ester in 70 ml ethanol were stirred with 50 ml 1.6 M NaOH at RT for 4 hrs. The mixture was diluted with dichloromethane and acidified with aqueous HCl to a pH of 1–2, then extracted with dichloromethane. The combined dichloromethane phases were extracted with 1 M NaOH, the aqueous phase was again acidified and once more extracted with dichloromethane. Evaporation of the solvent under vacuum yielded 5.0 g of the title product.

c) 6-(2,6-Dichloro-phenyl)-2-methylsulfanylpyrido[2,3-d]pyrimidine-7-carboxylic acid 3.0 g of the product from ex. b) were dissolved in 20 ml dry N,N-dimethylformamide (DMF) and cooled to −20° C. 2.55 g potassium tert-butylate were added slowly. At −10° C. 1.777 g of 4-amino-2-methylsulfanylpyrimidine-5-carbaldehyde were added and the mixture was warmed to 70° C. The resulting suspension was diluted with another 30 ml DMF and stirring at 70° C. was continued for 3 hrs.

The mixture was cooled to room temperature (RT) and diluted with 300 ml water. Upon acidification with HCl to pH 1–2 the crude product precipitated and was filtered off, and further purified by chromatography (silica, ethyl acetate+5% acetic acid). Yield 1.35 g of the title product.

d) 6-(2,6-Dichloro-phenyl)-2-methylsulfanylpyrido[2,3-d]pyrimidine-7-carboxylic acid (2-methanesulfonylamino-ethyl)-amide 0.45 g of the product of ex. c) were dissolved in 10 ml dry DMF, 0.215 g carbonyl diimidazole were added and the mixture was stirred at RT for 1 hr. 0.228 g 2-methylsulfonylamino-ethylamine in 4 ml DMF were added dropwise and the mixture stirred for another 2 hrs. The mixture was diluted with 200 ml water. Crude title product precipitated and was collected by filtration. The filtrate was extracted with dichloromethane, the organic phases dried and evaporated and the residue was combined with the first precipitate of crude product. Chromatography on silica yielded 375 mg of the title product.

e) 2-({[6-(2,6-Dichloro-phenyl)-2-methylsulfanyl-pyrido[2,3-d]pyrimidine-7-carbonyl]-amino}-methyl)-pyrrolidine-1-carboxylic acid tert-butyl ester Analogous to ex. d) from 0.2 g of starting material c), 0.096 g 1,1'-carbonyldiimidazole (CDI), and 0.153 g (R)-2-aminomethyl-1-Boc-pyrrolidine (purchased from Astatech).

The reaction mixture in DMF was diluted with 100 ml water and precipitated crude product isolated by filtration. The filtrate was acidified with HCl and extracted with dichloromethane. The crude precipitate from above was dissolved in dichloromethane and washed with dilute HCl, then combined with the other dichloromethane extracts. Evaporation and chromatography of the residue on silica yielded 152 mg of the title product.

f) 6-(2,6-Dichloro-phenyl)-2-methylsulfanyl-8H-pyrido[2,3-d]pyrimidin-7-one

To a mixture of 5.0 g 4-amino-2-methylsulfanylpyrimidine-5-carbaldehyde in 50 ml tetraline 10.91 g 2,6-dichlorophenylacetic acid, 10.76 g triethyl amine and 22.45 g pivaloyl chloride were sequentially added. The mixture was stirred at 190° C. for 30 min, then another 2.04 ml pivaloyl chloride were added. After 30 min, the next portion of 2.04 ml pivaloyl chloride were added and the temperature was raised to 195° C. After another 30 and 60 min, two more portions pivaloyl chloride were added and finally stirring was continued for another hour at 195° C.

Approximately 40 ml of the solvent were removed under vacuum, 100 ml ether were added and the precipitated crude product isolated by filtration. The crude product was washed with ether and water to yield 4.16 g of the title product.

g) Trifluoro-methanesulfonic acid 6-(2,6-dichlorophenyl)-2-methylsulfanyl-pyrido[2,3-d]pyrimidin-7-yl ester 4.0 g of starting material f) were suspended in 20 ml dry N-Methyl-2-pyrrolidone (NMP) and treated with 0.562 g of 60% sodium hydride. After stirring for 30 min at 40° C., the mixture was cooled to RT and 7.02 g N-phenyltrifluoromethansulfonimide were added. After 45 min at RT, another 2.01 g N-phenyltrifluoromethansulfonimide were added and stirring was continued for another 30 min.

The solvent was removed under vacuum at 60° C. and the residue purified by chromatography on silica to yield 5.38 g of the title product, containing ca. 25% N-phenyltrifluoromethansulfonamide. 2.4 g of this material were purified further by dissolving in dichloromethane and washing with aqueous sodium carbonate solution to give 1.72 g which were used in the next step.

h) 6-(2,6-Dichloro-phenyl)-2-methylsulfanyl-pyrido[2,3-d]pyrimidine-7-carbonitrile 1.72 g starting material g) from above were treated in 17.5 ml dry NMP with 0.423 g tetrakis-(triphenylphosphino)palladium(0) and 0.859 g zinc cyanide at 90° C. for 75 min. The solvent was evaporated under vacuum and the residue chromatographed on silica to yield 0.50 g of the title product.

Final Products

EXAMPLE 1

6-(2,6-Dichloro-phenyl)-2-(4-morpholin-4-yl-phenylamino)-pyrido[2,3-d]pyrimidine-7-carboxylic acid (pyrrolidin-2-ylmethyl)-amide 36 mg of 70% meta-chloroperbenzoic acid (mCPBA) were dissolved in 4 ml dichloromethane and the solution dried by filtration over sodium sulfate. The dried mCPBA solution was added to a solution of 75 mg of starting material e) in 4 ml dichloromethane at RT, and the oxidation reaction was monitored by TLC. After 1 hr starting material was consumed and excess mCPBA quenched by addition of a few drops of dimethylsulfide. 37 mg 4-morpholinoanilin were added and stirring was continued at RT for 14 hrs.

The mixture was diluted with dichloromethane and washed with 10% aqueous acetic acid. Evaporation of the organic phase and chromatography of the residue yielded 67 mg of Boc protected title product.

The above material was dissolved in 2 ml dichloromethane and stirred with 2 ml of a 2M solution of HCl in ether at RT for 3 hrs. The precipitate was isolated by filtration, dissolved in a small amount of methanol and diluted with a mixture of aqueous potassium bicarbonate and dichloromethane. The dichloromethane phase was separated, dried and evaporated to yield 41 mg of the title product.

¹H-NMR (CDCl3): 9.15 (s, 1H); 8.47 (br s, 1H); 7.95 (s, 1H); 7.69 (br m, 3H); 7.40 (d, 2H); 7.26 (t, 1H); 6.98 (d, 2H); 3.89 (t, 4H); 3.48 (m, 1H); 3.34 (m, 1H); 3.17 (m, 5H); 2.94 (m, 2H); 1.60–2.00 (m, 3H); 1.40 (m, 1H);

EXAMPLE 2

6-(2,6-Dichloro-phenyl)-2-[4-(4-methyl-piperazin-1-yl)-phenylamino]-pyrido[2,3-d]pyrimidine-7-carboxylic acid (2-methanesulfonylamino-ethyl)-amide Analogous to example 1, 50 mg of starting material d) were oxidized with 29 mg meta-chloroperbenzoic acid (mCPBA) in dichloromethane at RT.

22 mg 4-(4-methylpiperazino)aniline were added and the mixture was stirred 14 hrs at RT. After dilution with another 10 ml dichloromethane the mixture was washed with water, the organic phase dried and evaporated and further purified by chromatography on silica (dichloromethane 19/methanol 1/ammonia 0.5). Yield 44 mg of the title product.

¹H-NMR (CD3OD): 9.28 (s, 1H); 8.18 (s, 1H); 7.78 (br d, 2H); 7.48 (d, 2H); 7.36 (t, 1H); 7.03 (d, 2H); 4.60 (br s, 1H); 3.46 (t, 2H); 3.26 (t) and 3.22 (t, together 6H); 3.20 (s, 3H); 2.65 (t, 4H); 2.36 (s, 3H).

EXAMPLE 3

6-(2,6-Dichloro-phenyl)-2-[3-(2-hydroxy-ethylsulfanyl)-phenylamino]-pyrido[2,3-d]pyrimidine-7-carboxylic acid (2-methanesulfonylamino-ethyl)-amide 60 mg of starting material d) were oxidized with mCPBA analogous to example 1. 27 mg of 3-(2-hydroxyethylsulfanyl)aniline were added and the reaction mixture stirred for 15 hrs at RT. The mixture was diluted with 10 ml dichloromethane, washed with 10% aqueous acetic acid and dried and evaporated. Purification first by column chromatography on silica (dichloromethane/methanol), subsequently by preparative High Performance Liquid Chromatography coupled with Mass Spectrometry (HPLC-MS) and eventually by preparative Thin Layer Chromatography (TLC) on silica (dichlormethane/methanol) yielded 12 mg of the title product.

¹H-NMR (CDCl3): 9.21 (s, 1H); 8.91 (br s, 1H); 8.07 (s, 1H); 7.83 (br s, 1H); 7.77 (s, 1H); 7.43 (d, 2H); 7.31 (t, 1H); 7.25 (m, 1H); 7.05 (d, 1H); 6.85 (br s and d, 2H); 5.67 (br, 1H); 4.13 (m, 2H); 3.58 (m, 2H); 3.35 (m, 4H); 2.93 (s, 3H).

EXAMPLE 4

6-(2,6-Dichloro-phenyl)-2-[4-(2-hydroxy-ethoxy)-phenylamino]-pyrido[2,3-d]pyrimidine-7-carbonitrile 100 mg of starting material h) in 3.5 ml dichloromethane were treated with 301 mg 2-benzenesulfonyl-3-phenyl-oxaziridine at RT. After 5.5 hrs. excess oxidation reagent was quenched by addition of 70 mg dimethylsulfide. 265 mg 4-(2-hydroxyethyl)aniline in 2.5 ml NMP were added and the mixture was stirred at RT for 18.5 hrs.

The solvents were removed under vacuum and the residue chromatographed on silica to yield 220 mg crude product contaminated with excess aniline reagent. The crude product was dissolved in ethyl acetate and washed with dilute aqueous HCl. The organic phase was dried, evaporated, and the residue finally triturated with heptane to yield 94 mg of the title product.

¹H-NMR (CDCl3): 9.19 (s, 1H); 8.08 (s, 1H); 7.80 (br m, 2H); 7.63 (br s, 1H); 7.52 (d, 2H); 7.42 (t, 1H); 7.00 (d, 2H); 4.12 (m, 2H); 3.99 (m, 2H);

EXAMPLE 5

6-(2,6-Dichloro-phenyl)-2-[4-(2-hydroxy-ethoxy)-phenylamino]-pyrido[2,3-d]pyrimidine-7-carboxylic acid amide 20 mg of the product from example 3 in 1 ml THF were mixed with 13.5 mg potassium trimethylsilanolate under Ar atmosphere. The mixture was heated to 100° C. for 20 min in a microwave reactor.

The cooled reaction mixture was diluted with 0.1 ml water, and a small amount alumina chromatography material was added. This suspension was evaporated to dryness under vacuum and the residue was packed onto a silica chromatography column. Elution with ethyl acetate 6/heptane 1 gave 6 mg of the title product.

¹H-NMR (DMSO-d6): 10.24 (br s, 1H); 9.41 (s, 1H); 8.31 (s, 1H); 8.13 (br s, 1H); 7.92 (m, 2H); 7.56 (m, 3H); 7.42 (t, 1H); 6.99 (d, 2H); 4.87 (t, 1H); 4.00 (t, 2H); 3.73 (m, 2H)

EXAMPLE 6

Analogous to the procedure described in Example 1, but using the corresponding starting materials as described above, the following compounds can be obtained:

| Example-No. | Systematic Name | ¹H-NMR |
|---|---|---|
| 6-1 | 6-(2,6-Dichloro-phenyl)-2-[4-(2-hydroxy-ethoxy)-phenylamino]-pyrido[2,3-d]pyrimidine-7-carboxylic acid (2-hydroxy-ethyl)-amide | CDCl3: 9.15(s, 1H); 8.54(br s, 1H); 7.97(s, 1H); 7.87(br s, 1H); 7.64(m, 2H); 7.40(d, 2H); 7.26(t, 1H); 6.95(d, 2H); 4.08(t, 2H); 3.95(t, 2H); 3.74(t, 2H); 3.50(m, 2H); 1.86(br, 2H). |
| 6-2 | 6-(2,6-Dichloro-phenyl)-2-(4-morpholin-4-yl-phenylamino)-pyrido[2,3-d]pyrimidine-7-carboxylic acid (2-hydroxy-ethyl)-amide | CDCl3: 9.15(s, 1H); 8.54(br t, 1H); 7.97(s, 1H); 7.74(br s, 1H); 7.68(br m, 2H); 7.42(d, 2H); 7.27(t, 1H); 6.98(d, 2H); 5.50(br, 1H); 3.89(t, 4H); 3.77(t, 2H); 3.55(m, 2H); 3.16(t, 4H). |
| 6-3 | 6-(2,6-Dichloro-phenyl)-2-(4-morpholin-4-yl- | CDCl3: 9.15(s, 1H); 8.52(br t, 1H); 7.97(s, 1H); 7.80(br s, 1H); |

-continued

| Example-No. | Systematic Name | ¹H-NMR |
|---|---|---|
| | phenylamino)-pyrido[2,3-d]pyrimidine-7-carboxylic acid (2-methanesulfonylamino-ethyl)-amide | 7.69(br m, 2H); 7.41(d, 2H); 7.28(t, 1H); 6.98(d, 2H); 5.23(t, 1H); 3.89(t, 4H); 3.56(m, 2H); 3.34(m, 2H); 3.17(t, 4H); 2.92(s, 3H). |
| 6-4 | 6-(2,6-Dichloro-phenyl)-2-[4-(2-hydroxy-ethoxy)-phenylamino]-pyrido[2,3-d]pyrimidine-7-carboxylic acid (2-methanesulfonylamino-ethyl)-amide | CDCl3: 9.14(s, 1H); 8.50(br t, 1H); 7.96(s, 1H); 7.91(br s, 1H); 7.68(br m, 2H); 7.41(d, 2H); 7.28(t, 1H); 6.94(d, 2H); 5.39(t, 1H); 4.11(m, 2H); 3.97(t, 2H); 3.54(m, 2H); 3.33(m, 2H); 2.92(s, 3H). |
| 6-5 | 6-(2,6-Dichloro-phenyl)-2-[4-(2-hydroxy-ethoxy)-phenylamino]-pyrido[2,3-d]pyrimidine-7-carboxylic acid ((R)-1-pyrrolidin-2-ylmethyl)-amide | CDCl3: 9.16(s, 1H); 8.50(br s, 1H); 7.95(s, 1H); 7.85(br s, 1H); 7.70(br m, 2H); 7.40(d, 2H); 7.26(t, 1H); 6.97(d, 2H); 4.11(t, 2H); 3.98(t, 2H); 3.48(m, 1H); 3.34(m, 1H); 3.22(m, 1H); 2.93(m, 2H); 1.60–1.99(m, 3H); 1.41(m, 1H); |
| 6-6 | 6-(2,6-Dichloro-phenyl)-2-(3-methanesulfonylamino-phenylamino)-pyrido[2,3-d]pyrimidine-7-carboxylic acid (2-methanesulfonylamino-ethyl)-amide | CDCl3: 9.21(s, 1H); 8.57(t, 1H); 8.47(br s, 1H); 8.03(s, 1H); 7.98(br s, 2H); 7.42(d, 2H); 7.35(m, 3H); 7.13(m, 2H); 5.40(t, 1H); 3.54(m, 2H); 3.37(m, 2H); 3.06(s) and 3.02(s, together 6H). |
| 6-7 | 6-(2,6-Dichloro-phenyl)-2-(3-methylsulfanyl-phenylamino)-pyrido[2,3-d]pyrimidine-7-carboxylic acid(2-methanesulfonylamino-ethyl)-amide | CD3OD: 9.37(s, 1H); 8.27(s, 1H); 7.85(s, 1H); 7.80(d, 1H); 7.50(d, 2H); 7.39(d) and 7.34(t, together 2H); 7.05(d, 1H); 3.48(t, 2H); 3.28(t, 2H); 2.98(s, 3H); 2.56(s, 3H). |
| 6-8 | 6-(2,6-Dichloro-phenyl)-2-(6-methyl-pyridin-3-ylamino)-pyrido[2,3-d]pyrimidine-7-carboxylic acid(2-methanesulfonylamino-ethyl)-amide | CDCl3: 9.23(s, 1H); 8.84(s, 1H); 8.63(br t, 1H); 8.41(br s, 1H); 8.05(s, 1H); 7.41(d, 2H); 7.31(d) and 7.26(t, together 2H); 5.34(br s, 1H); 3.61(m, 2H); 3.38(m, 2H); 2.94(s, 3H); 2.58(s, 3H). |

EXAMPLE 7

Analogous to the procedure described in Example 4, but using the corresponding starting materials as described above, the following compounds can be obtained:

| Example-No. | Systematic Name | ¹H-NMR |
|---|---|---|
| 7-1 | 6-(2,6-Dichloro-phenyl)-2-[4-(2-diethylamino-ethoxy)-phenylamino]-pyrido[2,3-d]pyrimidine-7-carbonitrile | CDCl3: 9.18(br s, 1H); 8.07(s, 1H); 7.87(br m, 2H); 7.65(s, 1H); 7.52(d, 2H); 7.42(t, 1H); 6.97(d, 2H); 4.09(t, 2H); 2.91(t, 2H); 2.68(q, 4H); 1.09(t, 6H); |
| 7-2 | 6-(2,6-Dichloro-phenyl)-2-(4-morpholin-4-yl-phenylamino)-pyrido[2,3-d]pyrimidine-7-carbonitrile | CDCl3: 9.20(s, 1H); 8.08(s, 1H); 7.79(br m, 2H); 7.60(s, 1H); 7.55(d, 2H); 7.44(t, 1H); 7.01(d, 2H); 3.91(t, 4H); 3.20(t, 4H); |

EXAMPLE 8

Analogous to the procedure described in Example 5, but using the corresponding starting material as described above, the following compound can be obtained:

| Example-No. | Systematic Name | ¹H-NMR |
|---|---|---|
| 8-1 | 6-(2,6-Dichloro-phenyl)-2-(4-morpholin-4-yl-phenylamino)-pyrido[2,3-d]pyrimidine-7-carboxylic acid amide | DMSO-d6: 10.18(br s, 1H); 9.39(s, 1H); 8.29(s, 1H); 8.12(br s, 1H); 7.87(m, 2H); 7.55(m, 3H); 7.42(t, 1H); 6.99(d, 2H); 3.77(t, 4H); 3.10(t, 4H); |

The compounds of the invention described herein can be incorporated into pharmaceutical compositions suitable for administration. Such compositions typically comprise the compounds and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such carriers for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In some cases, the composition is sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, some methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration) the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to the achieved, and the limitations inherent in the art of compounding such an active compound for the treatment of individuals.

The pharmaceutical compositions can be included in a container, pack, or dispenser together with instructions for administration. Kits are contemplated which contain the therapeutic agents of the invention.

The compounds of the present invention may be used to treat or prevent diseases or conditions mediated by tyrosine kinase including, but not limited to, cancer, inflammatory or immunological diseases, central nervous system diseases, bone diseases, benign hyperplasia, transplant rejection, inflammatory bowel syndrome, rheumatoid arthritis, psoriasis, restenosis, allergic asthma, Alzheimer's disease, Parkinson disease, stroke, osteoporosis, cancer, and/or benign hyperplasias. In particular embodiments, the compounds are especially useful in the treatment or control of cancer.

Unless stated to the contrary, all compounds in the examples were prepared and characterized as described. All ranges recited herein include all combinations and subcombinations included within that range limit. All patents and publications cited herein are hereby incorporated by reference in their entirety.

The invention claimed is:
1. The compounds of formula I:

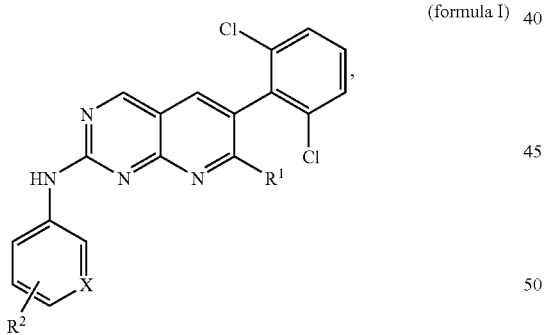

(formula I)

wherein:
R$^1$ is selected from the group consisting of:
  (a) —C(O)—NH-alkyl or —C(O)—N(alkyl)$_2$, wherein the alkyl groups of —C(O)—NH-alkyl or —C(O)—N(alkyl)$_2$ are optionally substituted with one or more constituents selected from the group consisting of:
    (1) —OH;
    (2) —NH(alkyl), wherein the alkyl group is optionally substituted with —OH;
    (3) —N(alkyl)$_2$, wherein the alkyl groups are optionally substituted with —OH;
    (4) —NH—C(O)-alkyl, wherein the alkyl group is optionally substituted with —OH;
    (5) —C(O)—NH-alkyl, wherein the alkyl group is optionally substituted with —OH;
    (6) —C(O)—N(alkyl)$_2$, wherein the alkyl groups are optionally substituted with —OH;
    (7) —C(O)—NH$_2$;
    (8) —O-alkyl, wherein the alkyl group is optionally substituted with —OH;
    (9) -heterocyclyl;
    (10) —NH-heterocyclyl;
    (11) —NH—S(O)$_2$-alkyl, wherein the alkyl group is optionally substituted with —OH;
    (12) —S(O)$_2$—NH$_2$; and
    (13) —S(O)-alkyl, wherein the alkyl group is optionally substituted with —OH;
  (b) —CN;
  (c) —C(O)—NH$_2$;
  (d) —C(O)—NH-heterocyclyl;
  (e) —C(O)—NH—NH—C(O)—NH$_2$; and
  (f) —C(O)—NH—NH—C(O)-alkyl, wherein the alkyl group is optionally substituted with —NH(alkyl) or —N(alkyl)$_2$;
R$^2$ is selected from the group consisting of:
  (a) halogen;
  (b) heterocyclyl;
  (c) alkyl, wherein the alkyl group is optionally substituted with one or more constituents selected from the group consisting of:
    (1) —OH;
    (2) —O-alkyl;
    (3) —NH-alkyl; and
    (4) —N(alkyl)$_2$;

(d) —NH—C(O)-alkyl, wherein the alkyl group is optionally substituted with one or more constituents selected from the group consisting of:
  (1) —OH;
  (2) —O-alkyl;
  (3) —NH-alkyl; and
  (4) —N(alkyl)$_2$;
(e) —NH—S(O)$_2$-alkyl, wherein the alkyl group is optionally substituted with one or more constituents selected from the group consisting of:
  (1) —OH;
  (2) —O-alkyl;
  (3) —NH-alkyl; and
  (4) —N(alkyl)$_2$;
(f) —(CH$_2$)$_m$—S(O)$_2$—NH$_2$;
(g) —(CH$_2$)$_m$—S(O)$_2$—N(alkyl)$_2$; wherein the alkyl groups are optionally substituted with one or more constituents selected from the group consisting of:
  (1) —OH;
  (2) —O-alkyl;
  (3) —NH-alkyl; and
  (4) —N(alkyl)$_2$;
(h) —(CH$_2$)$_m$—S(O)$_2$—NH-(alkyl), wherein the alkyl group is optionally substituted with one or more constituents selected from the group consisting of:
  (1) —OH;
  (2) —O-alkyl;
  (3) —NH-alkyl; and
  (4) —N(alkyl)$_2$;
(i) —O-alkyl, wherein the alkyl group is optionally substituted with one or more constituents selected from the group consisting of:
  (1) —OH;
  (2) —O-alkyl;
  (3) —NH-alkyl; and
  (4) —N(alkyl)$_2$; and
(j) —S(O)$_n$-alkyl, wherein the alkyl group is optionally substituted with one or more constituents selected from the group consisting of:
  (1) —OH;
  (2) —O-alkyl;
  (3) —NH-alkyl; and
  (4) —N(alkyl)$_2$;
x is —CH= or —N=;
m is 0, 1, 2, 3, 4, 5 or 6;
n is 0, 1 or 2;
and pharmaceutically acceptable salts thereof.

2. The compounds according to claim 1, wherein:
X is —CH=;
R$^1$ is —C(O)—NH-alkyl, wherein the alkyl group is optionally substituted with one or more constituents selected from the group consisting of:
  (a) —OH;
  (b) —NH(alkyl), wherein the alkyl group is optionally substituted with —OH;
  (c) —N(alkyl)$_2$, wherein the alkyl groups are optionally substituted with —OH;
  (d) —NH—C(O)-alkyl, wherein the alkyl group is optionally substituted with —OH;
  (e) —C(O)—NH-alkyl, wherein the alkyl group is optionally substituted with —OH;
  (f) —C(O)—N(alkyl)$_2$, wherein the alkyl groups are optionally substituted with —OH;
  (g) —C(O)—NH$_2$;
  (h) —O-alkyl, wherein the alkyl group is optionally substituted with —OH;
  (i) -heterocyclyl;
  (j) —NH-heterocyclyl;
  (k) —NH—S(O)$_2$-alkyl, wherein the alkyl group is optionally substituted with —OH;
  (l) —S(O)$_2$—NH$_2$; and
  (m) —S(O)-alkyl, wherein the alkyl group is optionally substituted with —OH.

3. The compounds according to claim 1, wherein:
X is —CH=;
R$^1$ is —C(O)—NH-methyl or —C(O)—NH-ethyl, wherein the methyl or ethyl group is unsubstituted or once substituted with a group selected from the group consisting of:
  (a) —OH;
  (b) -pyrrolidinyl; and
  (c) —NH—S(O)$_2$—CH$_3$.

4. The compounds according to claim 1, wherein:
X is —CH=;
R$^1$ is —C(O)—NH-ethyl or —C(O)—NH-methyl, wherein the methyl or ethyl group is once substituted with a group selected from the group consisting of:
  (a) —OH; and
  (b) -pyrrolidinyl;
R$^2$ is selected from the group consisting of:
  (a) morpholin-4-yl;
  (b) —NH—S(O)$_2$—CH$_3$;
  (c) —O-alkyl; wherein the alkyl group is optionally once substituted with a constituent selected from the group consisting of:
    (1) —OH;
    (2) —O-alkyl;
    (3) —NH-alkyl; and
    (4) —N(alkyl)$_2$; and
  (d) —S(O)$_n$-alkyl, wherein the alkyl group is optionally once substituted with a constituent selected from the group consisting of:
    (1) —OH;
    (2) —O-alkyl;
    (3) —NH-alkyl; and
    (4) —N(alkyl)$_2$;
n is 0, 1 or 2; and
pharmaceutically acceptable salts thereof.

5. The compounds according to claim 4 selected from the group consisting of:
6-(2,6-Dichloro-phenyl)-2-[4-(2-hydroxy-ethoxy)-phenylamino]-pyrido[2,3-d]pyrimidine-7-carboxylic acid (2-hydroxy-ethyl)-amide;
6-(2,6-Dichloro-phenyl)-2-(4-morpholin-4-yl-phenylamino)-pyrido[2,3-d]pyrimidine-7-carboxylic acid (2-hydroxy-ethyl)-amide;
6-(2,6-Dichloro-phenyl)-2-[4-(2-hydroxy-ethoxy)-phenylamino]-pyrido[2,3-d]pyrimidine-7-carboxylic acid ((R)-1-pyrrolidin-2-ylmethyl)-amide; and
6-(2,6-Dichloro-phenyl)-2-(4-morpholin-4-yl-phenylamino)-pyrido[2,3-d]pyrimidine-7-carboxylic acid ((R)-1-pyrrolidin-2-ylmethyl)-amide.

6. The compounds according to claim 1, wherein:
X is —CH=;
R$^1$ is —C(O)—NH—(CH$_2$)$_2$—NH—S(O)$_2$—CH$_3$;
R$^2$ is is selected from the group consisting of:
  (a) morpholin-4-yl;
  (b) 4-methyl-piperazin-1-yl;
  (c) —NH—S(O)$_2$—CH$_3$;
  (d) —O-alkyl; wherein the alkyl group is optionally once substituted with a constituent selected from the group consisting of:

(1) —OH;
(2) —O-alkyl;
(3) —NH-alkyl; and
(4) —N(alkyl)$_2$; and
(e) —S(O)$_n$-alkyl, wherein the alkyl group is optionally once substituted with a constituent selected from the group consisting of:
(1) —OH;
(2) —O-alkyl;
(3) —NH-alkyl; and
(4) —N(alkyl)$_2$;

n is 0, 1 or 2; and pharmaceutically acceptable salts thereof.

7. The compounds according to claim 6 selected from the group consisting of:
- 6-(2,6-Dichloro-phenyl)-2-(4-morpholin-4-yl-phenylamino)-pyrido[2,3-d]pyrimidine-7-carboxylic acid (2-methanesulfonylamino-ethyl)-amide;
- 6-(2,6-Dichloro-phenyl)-2-[4-(2-hydroxy-ethoxy)-phenylamino]-pyrido[2,3-d]pyrimidine-7-carboxylic acid (2-methanesulfonylamino-ethyl)-amide;
- 6-(2,6-Dichloro-phenyl)-2-(3-methanesulfonylamino-phenylamino)-pyrido[2,3-d]pyrimidine-7-carboxylic acid (2-methanesulfonylamino-ethyl)-amide;
- 6-(2,6-Dichloro-phenyl)-2-[3-(2-hydroxy-ethylsulfanyl)-phenylamino]-pyrido[2,3-d]pyrimidine-7-carboxylic acid (2-methanesulfonylamino-ethyl)-amide;
- 6-(2,6-Dichloro-phenyl)-2-[4-(4-methyl-piperazin-1-yl)-phenylamino]-pyrido[2,3-d]pyrimidine-7-carboxylic acid (2-methanesulfonylamino-ethyl)-amide; and
- 6-(2,6-Dichloro-phenyl)-2-(3-methylsulfanyl-phenylamino)-pyrido[2,3-d]pyrimidine-7-carboxylic acid (2-methanesulfonylamino-ethyl)-amide.

8. The compounds according to claim 1, wherein:
X is —CH═;
R$^1$ is —C(O)—NH$_2$;
R$^2$ is selected from the group consisting of:
(a) morpholin-4-yl;
(b) —NH—S(O)$_2$—CH$_3$;
(c) —O-alkyl, wherein the alkyl group is optionally once substituted with a constituent selected from the group consisting of:
(1) —OH;
(2) —O-alkyl;
(3) —NH-alkyl; and
(4) —N(alkyl)$_2$;
(d) —S(O)$_n$-alkyl, wherein the alkyl group is optionally once substituted with a constituent selected from the group consisting of:
(1) —OH;
(2) —O-alkyl;
(3) —NH-alkyl; and
(4) —N(alkyl)$_2$;

n is 0, 1 or 2; and pharmaceutically acceptable salts thereof.

9. The compounds according to claim 8 selected from the group consisting of:
- 6-(2,6-Dichloro-phenyl)-2-(4-morpholin-4-yl-phenylamino)-pyrido[2,3-d]pyrimidine-7-carboxylic acid amide; and
- 6-(2,6-Dichloro-phenyl)-2-[4-(2-hydroxy-ethoxy)-phenylamino]-pyrido[2,3-d]pyrimidine-7-carboxylic acid amide.

10. The compounds according to claim 1, wherein:
X is —CH═;
R$^1$ is —CN;
R$^2$ is selected from the group consisting of:
(a) morpholin-4-yl;
(b) —NH—S(O)$_2$—CH$_3$;
(c) —O-alkyl; wherein the alkyl group is optionally once substituted with a constituent selected from the group consisting of:
(1) —OH;
(2) —O-alkyl;
(3) —NH-alkyl; and
(4) —N(alkyl)$_2$;
(d) —S(O)$_n$-alkyl, wherein the alkyl group is optionally once substituted with a constituent selected from the group consisting of:
(1) —OH;
(2) —O-alkyl;
(3) —NH-alkyl; and
(4) —N(alkyl)$_2$;

n is 0, 1 or 2; and pharmaceutically acceptable salts thereof.

11. The compounds according to claim 10 selected from the group consisting of:
- 6-(2,6-Dichloro-phenyl)-2-[4-(2-diethylamino-ethoxy)-phenylamino]-pyrido[2,3-d]pyrimidine-7-carbonitrile;
- 6-(2,6-Dichloro-phenyl)-2-(4-morpholin-4-yl-phenylamino)-pyrido[2,3-d]pyrimidine-7-carbonitrile; and
- 6-(2,6-Dichloro-phenyl)-2-[4-(2-hydroxy-ethoxy)-phenylamino]-pyrido[2,3-d]pyrimidine-7-carbonitrile.

12. The compounds according to claim 1, wherein:
X is —N═;
R$^1$ is —C(O)—NH—(CH$_2$)$_2$—NH—S(O)$_2$—CH$_3$;
R$^2$ is selected from the group consisting of:
(a) alkyl;
(b) —NH—S(O)$_2$—CH$_3$;
(c) —O-alkyl; wherein the alkyl group is optionally substituted with a constituent selected from the group consisting of:
(1) —OH;
(2) —O-alkyl;
(3) —NH-alkyl; and
(4) —N(alkyl)$_2$; and
(d) —S(O)$_n$-alkyl, wherein the alkyl group is optionally substituted with a constituent selected from the group consisting of:
(1) —OH;
(2) —O-alkyl;
(3) —NH-alkyl; and
(4) —N(alkyl)$_2$;

n is 0, 1 or 2; and pharmaceutically acceptable salts thereof.

13. A compound according to claim 12, wherein the compound is:
- 6-(2,6-Dichloro-phenyl)-2-(6-methyl-pyridin-3-ylamino)-pyrido[2,3-d]pyrimidine-7-carboxylic acid (2-methanesulfonylamino-ethyl)-amide.

14. A process for the manufacture of the compounds of formula (I) according to claim 1 comprising:
(a) converting the carboxylic group in the compounds of general formula (II)

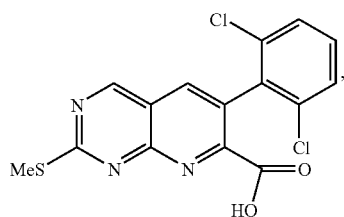

formula (II)

into the corresponding amides of formula (V)

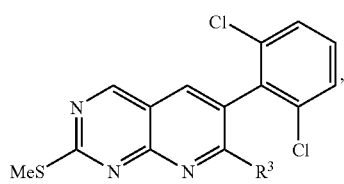

formula (V)

wherein
R³ is selected from the group consisting of:
(a) —C(O)—NH-alkyl or —C(O)—N(alkyl)₂, wherein the alkyl groups of —C(O)—NH-alkyl or —C(O)—N(alkyl)₂ are optionally substituted with one or more constituents selected from the group consisting of:
(1) —OH;
(2) —NH(alkyl), wherein the alkyl group is optionally substituted with —OH;
(3) —N(alkyl)₂, wherein the alkyl groups are optionally substituted with —OH;
(4) —NH—C(O)-alkyl, wherein the alkyl group is optionally substituted with —OH;
(5) —C(O)—NH-alkyl, wherein the alkyl group is optionally substituted with —OH;
(6) —C(O)—N(alkyl)₂, wherein the alkyl groups are optionally substituted with —OH;
(7) —C(O)—NH₂;
(8) —O-alkyl, wherein the alkyl group is optionally substituted with —OH;
(9) -heterocyclyl;
(10) —NH-heterocyclyl;
(11) —NH—S(O)₂-alkyl, wherein the alkyl group is optionally substituted with —OH;
(12) —S(O)₂—NH₂; and
(13) —S(O)-alkyl, wherein the alkyl group is optionally substituted with —OH;
(b) —C(O)—NH₂;
(c) —C(O)—NH-heterocyclyl;
(d) —C(O)—NH—NH—C(O)—NH₂; and
(e) —C(O)—NH—NH—C(O)-alkyl, wherein the alkyl group is optionally substituted with —NH(alkyl) or —N(alkyl)₂; and
(b) converting the methylthio group in the compounds of the general formula (V) into the corresponding sulfoxides of formula (VI)

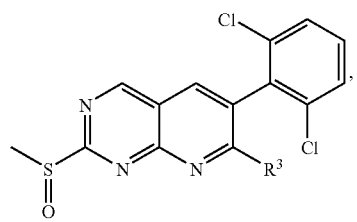

formula (VI)

wherein R³ is the same as defined in step (a);
(c) substituting the sulfoxide group of formula (VI) by the respective anilines of formula (II-A)

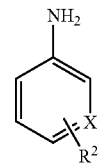

formula (II-A)

wherein R² and X have the meanings given for formula (I) in claim 1,
to give the corresponding compounds of formula (Ia);

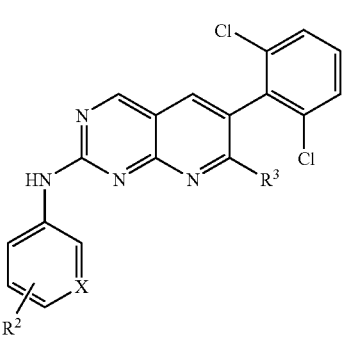

formula (Ia)

wherein R³ is the same as defined in step (a);
and R² and X have the meanings given for formula (I) in claim 1
(d) optionally converting a primary amide derivative of formula (Ia) obtained from step (c) into its corresponding 7-carbonitril derivative of formula (I) according to claim 1; and
(e) optionally converting said compound of formula (I), obtained from steps (c) or (d), into a pharmaceutically acceptable salt.

15. A pharmaceutical composition comprising a compound of claim 1 and a pharmaceutically acceptable carrier.

16. The pharmaceutical composition of claim 15 further comprising an adjuvant.

* * * * *

SEQUENCE LISTING

<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Glu Glu Glu Ile Tyr Gly Glu Phe Glu Ala Lys Lys Lys Lys
 1               5                  10                  15

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Aminocaprylic acid

<400> SEQUENCE: 2

Gly Xaa Ala Glu Glu Glu Ile Tyr Gly Glu Phe Glu Ala Lys Lys Lys
 1               5                  10                  15

Lys